(12) United States Patent
Van Hove et al.

(10) Patent No.: US 8,000,532 B2
(45) Date of Patent: Aug. 16, 2011

(54) DIGITAL PEN TO CAPTURE DATA IN AMBULATORY MONITORED PATIENTS

(75) Inventors: Jos W. Van Hove, Schiedam (NL); Willem Boute, Brummen (NL)

(73) Assignee: Medtronic, Inc., Minneapolis, MN (US)

( * ) Notice: Subject to any disclaimer, the term of this patent is extended or adjusted under 35 U.S.C. 154(b) by 983 days.

(21) Appl. No.: 11/681,864

(22) Filed: Mar. 5, 2007

(65) Prior Publication Data
US 2008/0208007 A1 Aug. 28, 2008

Related U.S. Application Data

(60) Provisional application No. 60/892,034, filed on Feb. 28, 2007.

(51) Int. Cl.
*G06K 9/00* (2006.01)
*G06K 9/22* (2006.01)

(52) U.S. Cl. ........................................ 382/187; 382/314

(58) Field of Classification Search .......... 382/187–189, 382/305, 314, 151; 705/2–5
See application file for complete search history.

(56) References Cited

U.S. PATENT DOCUMENTS

| | | | |
|---|---|---|---|
| 5,354,319 A | 10/1994 | Wyborny et al. | |
| 5,577,135 A | 11/1996 | Grajski et al. | |
| 5,596,698 A | 1/1997 | Morgan | |
| 5,724,985 A * | 3/1998 | Snell et al. | 600/510 |
| 5,778,882 A * | 7/1998 | Raymond et al. | 600/513 |
| 5,987,352 A | 11/1999 | Klein et al. | |
| 6,250,309 B1 | 6/2001 | Krichen et al. | |
| 6,333,995 B1 * | 12/2001 | Perrone | 382/187 |
| 6,418,346 B1 | 7/2002 | Nelson et al. | |
| 6,442,433 B1 | 8/2002 | Linberg | |
| 6,480,745 B2 | 11/2002 | Nelson et al. | |
| 6,482,154 B1 | 11/2002 | Haubrich et al. | |
| 6,522,915 B1 | 2/2003 | Ceballos et al. | |
| 6,574,511 B2 | 6/2003 | Lee | |
| 6,599,250 B2 | 7/2003 | Webb et al. | |
| 6,804,445 B2 | 10/2004 | Edlinger et al. | |
| 7,039,560 B2 * | 5/2006 | Kawatahara et al. | 702/187 |
| 7,043,305 B2 | 5/2006 | KenKnight et al. | |
| 2002/0004729 A1 | 1/2002 | Zak et al. | |
| 2002/0111540 A1 * | 8/2002 | Schmidt et al. | 600/300 |
| 2004/0122294 A1 | 6/2004 | Hatlestad et al. | |
| 2004/0243439 A1 * | 12/2004 | Huggard et al. | 705/2 |
| 2005/0024346 A1 | 2/2005 | Dupraz et al. | |
| 2005/0108054 A1 | 5/2005 | Gottlieb et al. | |
| 2005/0207823 A1 | 9/2005 | Adams et al. | |
| 2007/0008304 A1 * | 1/2007 | Tobin | 345/179 |
| 2007/0016453 A1 * | 1/2007 | Hiyama et al. | 705/3 |

* cited by examiner

*Primary Examiner* — Daniel Mariam

(57) ABSTRACT

A medical device system and method for monitoring a patient include a monitoring device for storing data relating to the patient and a digital pen for digitizing and storing data handwritten by the patient. A control module is configured to aggregate data stored by the monitoring device and handwritten data stored by the digital pen.

18 Claims, 5 Drawing Sheets

DIGITAL PEN TO CAPTURE DATA IN AMBULATORY MONITORED PATIENTS

CROSS REFERENCE TO PRIORITY APPLICATION

This application claims priority to application Ser. No. 60/892,034, filed Feb. 28, 2007 and entitled, "Digital Pen to Capture Data in Ambulatory Monitored Patients", which is incorporated by reference herein.

TECHNICAL FIELD

The invention relates generally to medical device systems for monitoring patients and, in particular, to a medical monitoring system including a digital pen for capturing handwritten data.

BACKGROUND

Numerous medical monitoring devices are available for monitoring physiological signals in an ambulatory patient. Such devices may be implantable devices, including ECG monitors, hemodynamic monitors, and insulin monitors, or external devices such as Holter monitors. Some devices provided for monitoring physiological signals may also be capable of delivering a therapy to the patient, such as an electrical stimulation therapy or a drug therapy, when the device determines there is a need for therapy based on the monitored physiological signal. Examples of such devices include cardiac pacemakers, implantable cardioverter defibrillators (ICDs), neurostimulators, drug pumps and insulin pumps.

Patients having such devices may be asked by their physician to keep a diary of symptoms associated with a medical condition to aid the physician in identifying the cause of such symptoms using physiological data stored by the monitoring device. Patients may not always be fully compliant in keeping such diaries. Moreover, the task of correlating written records with physiological data stored by the monitoring device can be burdensome.

Some implantable medical device systems include a handheld device operable by the patient to send signals to the implanted device. This handheld device, sometimes referred to as a "patient activator", allows a patient to transmit a signal to the monitoring device when the patient experiences symptoms relating to a medical condition. Upon receipt of the patient activator signal, the monitoring device may trigger storage of data and/or deliver or adjust a therapy. Typically a patient activator is provided with one or more buttons which the patient depresses to transmit a signal. The specificity of the information transferred to the monitoring device is limited. A signal may be transmitted to the monitoring device indicating that the patient is experiencing a symptom(s) without specific information regarding what symptom(s) were experienced or the severity of such symptoms. Limitations remain in presently available ambulatory patient monitoring systems relating to the recordation of patient symptoms or other handwritten medical data and the integration of such handwritten data with data stored automatically by a monitoring device.

DETAILED DESCRIPTION

Figure 1:
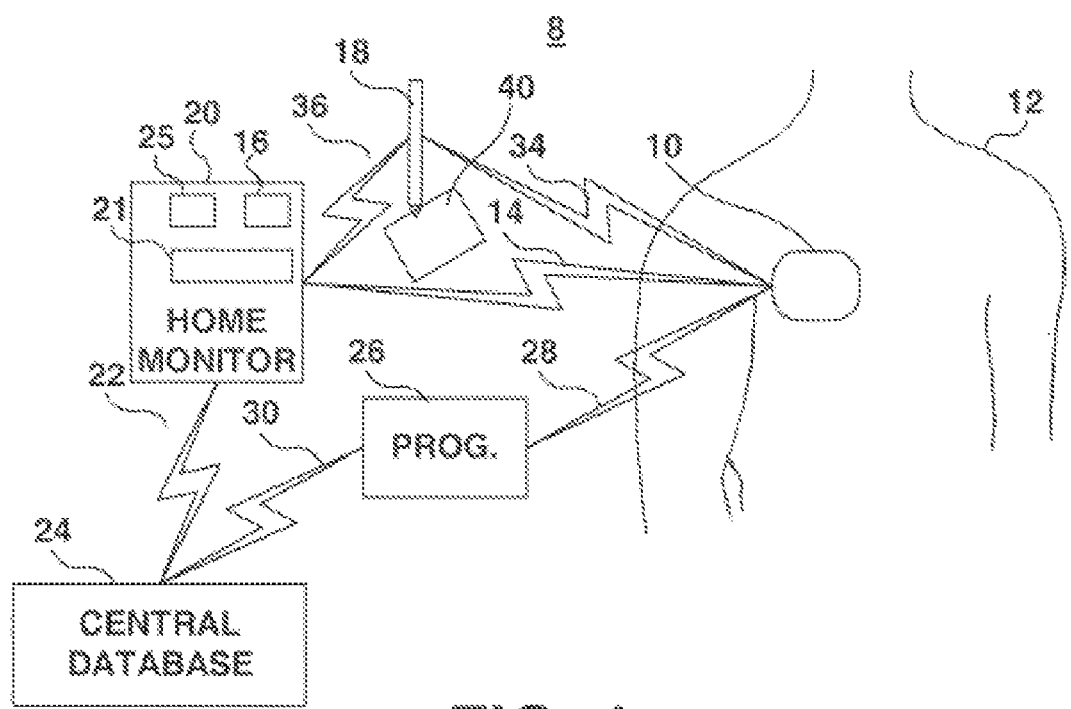
FIG. 1 is a schematic diagram of one patient monitoring system including a digital pen for capturing handwritten medical data.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic diagram of one patient monitoring system 8 including a digital pen for capturing handwritten medical data. The monitoring system 8 includes an implantable medical device (IMD) 10 adapted for implantation in a patient 12, digital pen 18, a home monitor 20, a programmer 26, and a networked central database 24. As used herein, "digital pen" refers to a handwriting instrument capable of capturing and storing data corresponding to handwritten information or gestures. Though not specifically shown in FIG. 1, a monitoring system may further include a patient activator for use by the patient to trigger certain IMD functions. The simplified illustration of IMD 10 in FIG. 1 may represent a variety of IMDs such as cardiac pacemakers, implantable cardioverter defibrillators, implantable cardiac monitors which may include both hemodynamic monitors and ECG recorders, drug delivery devices, insulin monitors or pumps, or neurostimulators.

In one embodiment, IMD 10 is provided as a subcutaneous monitoring device having physiological sensors, such as electrodes for monitoring electrical signals, incorporated on the IMD housing or positioned on subcutaneous leads extending from the IMD 10. Examples of subcutaneous monitoring devices are generally disclosed in U.S. Pat. No. 6,522,915 issued to Ceballos et al., and U.S. Pat. No. 5,987,352 issued to Klein et al, both of which patents are incorporated herein by reference in their entirety. IMD 10 may alternatively be coupled to one or more leads or fluid delivery catheters deployed to desired monitoring sites. For example one or more leads may be positioned in operative relation to chambers of the patient's heart or at other locations along the cardiovascular and/or respiratory system. Leads may be used for carrying electrodes or other physiological sensors used for monitoring one or more physiological conditions and delivering electrical stimulation or other therapies.

IMD 10 is provided with a telemetry module, as will be described below, for establishing a communication link 14 with home monitor 20, communication link 34 with digital pen 18, and communication link 28 with programmer 26. IMD 10 is typically a programmable device configured to receive operating programs and control parameters from programmer 26 and transfer device-related and patient-related data to programmer 26 upon receiving an interrogation command from programmer 26. Programmer 26 is typically used in a clinic or other medical facility by trained medical personnel. Home monitor 20 may be embodied as a tabletop, handheld, or wearable device and is configured with a telemetry module 16 for retrieving data from IMD 10 and optionally performing programming operations, which may be a limited set of programming operations as compared to programmer 26.

Home monitor 20 and programmer 26 are configured to communicate with central database 24 via a communication network to allow transfer of data received from IMD 10 to the central database 24 for remote patient monitoring. A central database 24 may be an Internet-based or other networked database used for remotely retrieving and reviewing data acquired by the IMD 10 and digital pen 18. Home monitor 20 transfers/receives data to/from central database 24 via a communication link 22, which is established via the Internet, a local area network, a wide area network, a telecommunications network or other appropriate communications network and may be a wireless communication link. Programmer 26 communicates with central database 24 via link 30. Examples of remote patient monitoring systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety.

Digital pen 18 is provided to patient 12 for use in recording symptoms experienced by the patient or other descriptive medical information such as when medications are taken, patient weight, blood pressure or data from other external equipment used to assess or measure physiological parameters, daily activities, or any other information requested by a clinician or considered medically significant by the patient. A "digital pen", as used herein, refers to a writing instrument enabled to digitally capture information handwritten by the patient. "Handwritten" as used herein refers to information or data that is originally written by a user using the digital pen. The handwritten data may or may not be written with ink or another writing medium that creates an actual visual image on paper. As such, "handwritten data" as used herein also refers to data that was "written" by a user making handwriting strokes or gestures using the digital pen without creating an actual visual image of the handwritten data that is readable by the user.

Digital pen 18 may be used in conjunction with specially designed paper 40. Paper 40 may be preprinted with a custom pattern for use in creating a digital image of written information. As will be further described below, paper 40 may be specially formatted for use in capturing handwritten medical information. Digital pens used with special paper are commercially available from Anoto AB, Lund Sweden and Logitech, Fremont, Calif. In other embodiments, digital pen 18 does not require the use of custom paper. A digital pen available from EPOS, Hod Hasharon, Israel, is usable with any type of paper. Examples of digital pens that may be adapted for use in embodiments of the present invention are generally disclosed in U.S. Pat. Application Publication No. 2005/0207823 to Adams et. al. and U.S. Pat. Application Publication No. 2005/0024346 to Dupraz et al., both of which are incorporated herein by reference in their entirety.

Handwritten information collected by digital pen 18 is available for transmission to IMD 10, home monitor 20 for further transmission to central database 24, or to another networked device such as a printer, personal computer, cellular phone, personal digital assistant (PDA) or the like. A communication system including an IMD and other communication devices such as a cellular phone, PDA, etc. is generally disclosed in U.S. Pat. No. 6,804,558 to Hailer et al., hereby incorporated herein by reference in its entirety. Handwritten data acquired by digital pen 18 is aggregated with data acquired by IMD 10 such that data automatically stored by IMD 10 can be correlated to the occurrence of symptoms, patient activity, patient medications, or other handwritten information acquired by digital pen 18.

Data aggregation is performed by a control module, which may be included in IMD 10. Aggregated data may be transferred to home monitor 20 via link 14. Alternatively, data aggregation may be performed by home monitor 20 or central database 24 after receiving data from both digital pen 18 and IMD 10. It is recognized that digital pen 18 may be enabled for communication with central database 24 and programmer 26. These additional communication links are not shown in FIG. 1 for the sake of clarity.

While the monitoring system 8 shown in FIG. 1 includes an IMD, other embodiments of the invention may include external monitoring devices. In some embodiments, home monitor 20 may be embodied as a beside or wearable device including one or more physiological sensors 25 that may be coupled to the patient, for example a blood pressure cuff, ECG electrodes, blood oxygen sensors, pulse pressure sensors or the like. As such, home monitor 20 may be embodied as an external ambulatory monitoring device used for acquiring physiological data directly from the patient using external physiological sensors 25 coupled to the patient.

Digital pen 18 may be configured for bidirectional communication with home monitor 20 such that written information recorded by digital pen 18 may be transmitted directly to home monitor 20 via communication link 36. Communication link 36 may be a wireless link, for example using Bluetooth technology, or a hardwired link, for example using a USB port. Home monitor 20 includes a control module 21 for controlling communication operations of home monitor 20 and in some embodiments for aggregating data acquired from IMD 10, physiological sensor 25 (if present), and digital pen 18. Such aggregated data may then be transferred to central database 24 for unified presentation to a clinician.

Figure 2:
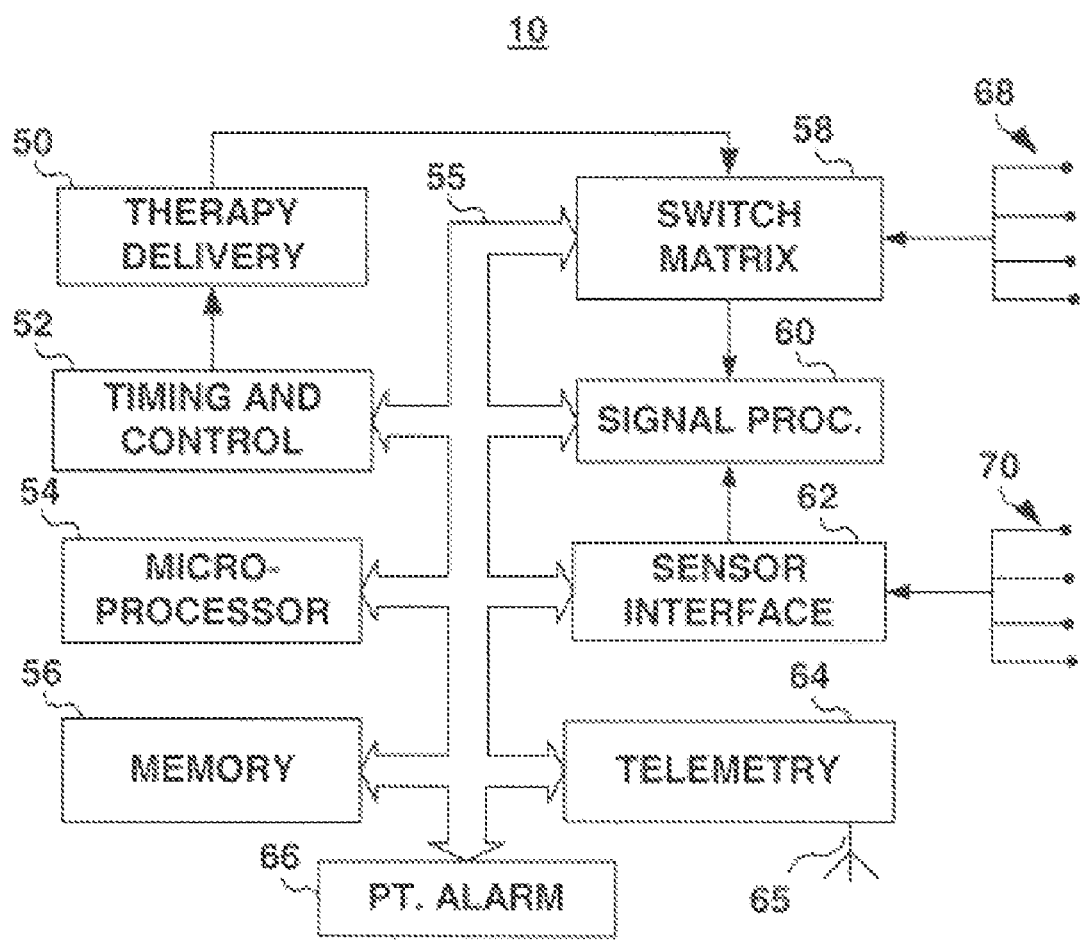
FIG. 2 is a block diagram of typical functional components of an implantable medical device (IMD).

FIG. 2 is a block diagram of typical functional components of an IMD, such as IMD 10 shown in FIG. 1. IMD 10 generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may also be used for sensing electrical signals within the body, such as cardiac signals, or for measuring impedance. In the case of cardiac stimulation devices, cardiac electrical signals are sensed for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias and monitoring for pathological changes in the ECG such as ST segment changes, T-wave morphological changes, QT interval measurements, etc. In other embodiments, electrodes 68 may be used for measuring impedance signals for monitoring edema, respiration or heart chamber volume. Impedance signals can also be used for monitoring lead performance.

IMD 10 may additionally or alternatively be coupled to one or more physiological sensors 70. Such sensors may include pressure sensors, accelerometers, flow sensors, blood chemistry sensors, activity sensors, impedance based sensors for respiratory, cardiac or pulmonary fluid assessment or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, pulmonary fluid accumulation, or patient activity. Monitored signals may be used for sensing the need for delivering a therapy under control of the operating system.

The operating system includes associated memory 56 for storing a variety of programmed-in operating mode and parameter values that are used by microprocessor 54. The memory 56 may also be used for storing data compiled from sensed physiological signals and/or relating to device operating history, including data relating to delivered therapies, for telemetry out on receipt of a retrieval or interrogation instruction. Memory 56 is used to store operating commands and data for controlling device operation and acquired data for later retrieval for use in diagnosing device function or patient condition. Memory 56 may further be used for storing data received by IMD 10 from digital pen 18.

Microprocessor 54 may execute device diagnostic algorithms to evaluate device performance. Such diagnostic operations may include predicting end of battery life, measuring lead impedances, measuring sensing thresholds, or the like. Device diagnostic data may be stored in memory 56 for use in evaluating device performance.

IMD 10 further includes telemetry circuitry 64 and antenna 65. Programming commands or data are transmitted during uplink or downlink telemetry between IMD telemetry circuitry 64 and external telemetry circuitry included in digital pen 18, programmer 26 or home monitor 20 (shown in FIG. 1). Examples of telemetry circuitry used in IMDs are generally disclosed in U.S. Pat. No. 5,354,319 issued to Wyborny et al. and in U.S. Pat. No. 6,482,154 issued to Haubrich et al., both of which are incorporated herein by reference in their entirety. The Haubrich '154 patent generally discloses a long-distance telemetry system that could be adapted for use in establishing communication links between ad digital pen and IMD 10.

IMD 10 may optionally be equipped with patient alarm circuitry 66 for generating audible tones, a perceptible vibration, muscle stimulation or other sensory stimulation for notifying the patient that a patient alert condition has been detected by IMD 10. Alternatively, the alarm may be transmitted to a patient activator, home monitor or other external equipment that is part of the monitoring system.

Figure 3:
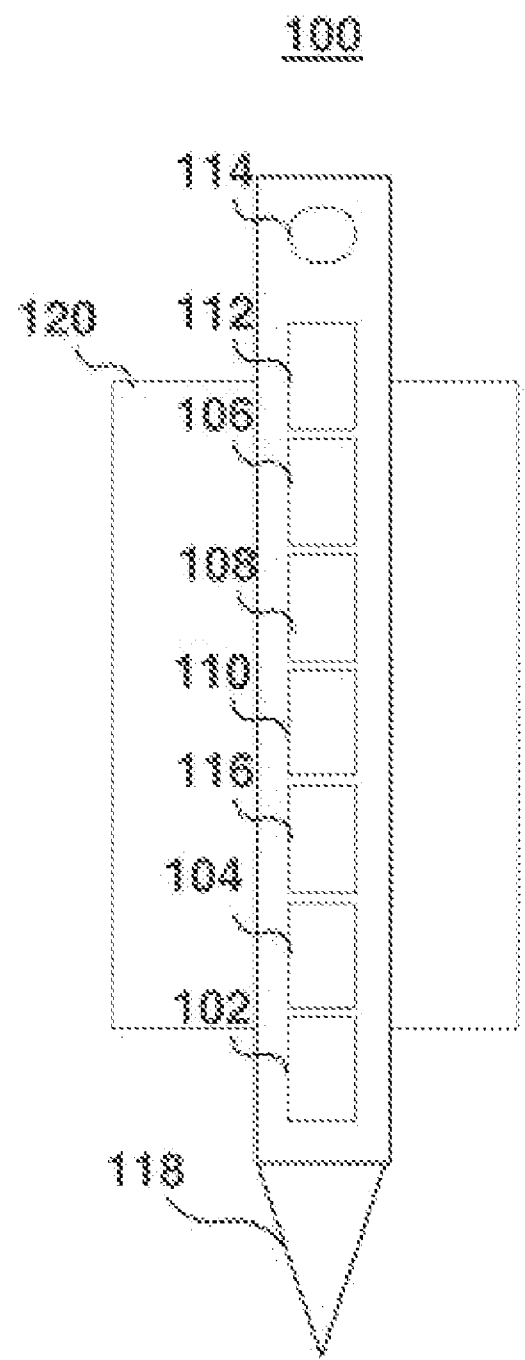
FIG. 3 is a schematic block diagram of a digital pen for use in a patient monitoring system.

FIG. 3 is a schematic block diagram of a digital pen for use in a patient monitoring system. Digital pen 100 includes a control module 102 for capturing and digitizing handwritten data and associated memory 104 for storing digitized data. Control module 102 may be enabled to execute handwriting recognition software which automatically converts digitized handwritten data into standard ASCII format or other suitable character encoded format, which is readable by the associated medical device operating system, in order to reduce the amount of data to be transmitted from digital pen 100 to a medical device. Pen 100 further includes a telemetry module 106 configured for bidirectional communication with a medical device, which may be an external and/or implantable device. Telemetry module 106 is used for transmitting digitized handwritten data to another medical device for aggregation with data automatically acquired by either an external or implanted monitoring device. Telemetry module 106 may correspond to a distance telemetry system as described in the above-incorporated Haubrich patent, Bluetooth or other wireless technology, or hardwired technology using, for example, USB ports. Telemetry module 106 may fully implemented within pen 18 or may be partially implemented in a cradle 120 for engaging pen 100.

Digital pen 100 further includes a real-time clock 108 allowing the time and date of digitized data to be logged such that handwritten data can be chronologically correlated with data automatically acquired by the monitoring device. Digital pen 100 includes a battery 110 for powering digital pen functions. Battery 110 may be a rechargeable battery with charging occurring when pen 100 is docked in cradle 120. Digital pen 100 may further include a light source 112 that allows the patient to easily locate pen 100 in the dark, for example during the night, and see what he/she is writing. A patient feedback indicator 114, such as an LED, may be provided to communicate to the patient the status of pen 100. For example, the LED may indicate the pen has been enabled and is collecting or transmitting data, or the LED may indicate battery status. Digital pen 100 may include an ink cartridge 116 for creating an actual visual image of handwritten data readable by the user. A writing nib 118 is provided at one end of pen 100.

Figure 4:
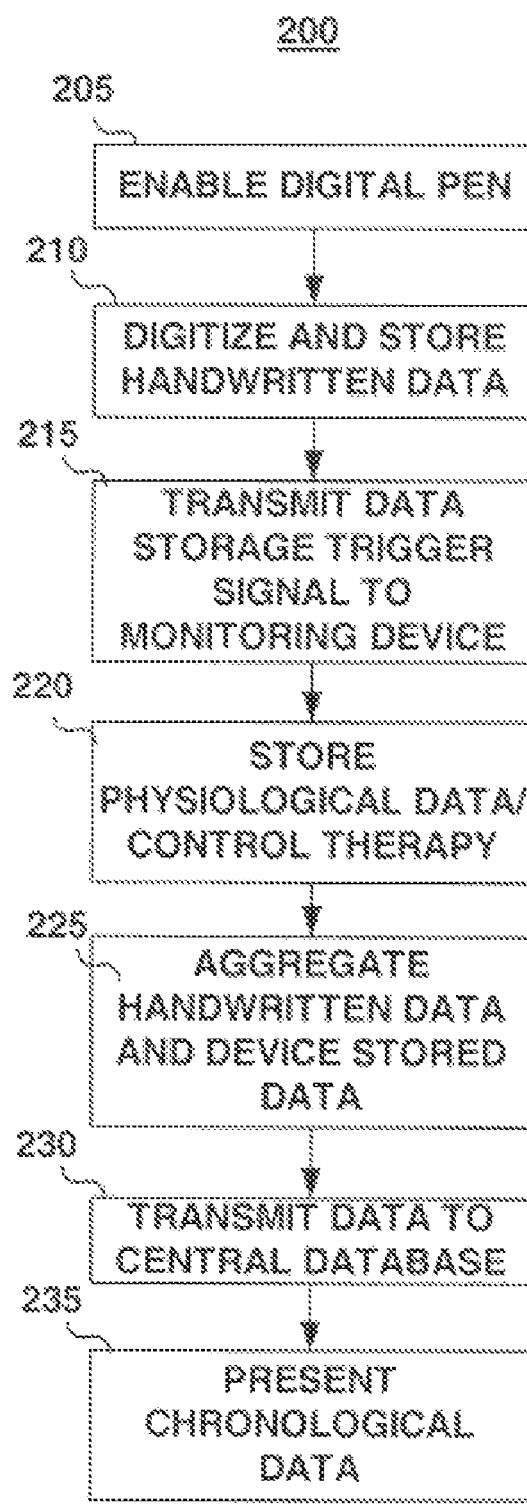
FIG. 4 is a flow chart of a method for acquiring data in a patient monitoring system.

FIG. 4 is a flow chart of a method for acquiring data in a patient monitoring system. Flow chart 200 is intended to illustrate the functional operation of the device, and should not be construed as reflective of a specific form of software or hardware necessary to practice the invention. It is believed that the particular form of software will be determined primarily by the particular system architecture employed in the monitoring device system and by the particular sensing and therapy delivery methodologies employed by the device. Providing software to accomplish the present invention in the context of any modern medical monitoring device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 200 begins at block 205 when the digital pen is enabled. A user may enable the digital pen by removing its cap or by actuating a switch or other mechanism. The digital pen is powered up and enabled for capturing and digitizing handwriting images. At block 210, handwritten data are captured, transformed into ASCII (or another suitable format) using dedicated handwriting recognition software, and stored by the digital pen. Handwritten data may correspond to a list of one or more symptoms experienced by the patient and may include an indication of the severity of the symptom. The time and date are stored with the handwritten data to allow aggregation of handwritten data with data automatically stored by the monitoring device. In some embodiments, the handwritten data may include a time that the symptom occurred. The patient may not always be able to record a symptom at exactly the time that the symptom is occurring. Accordingly, in some embodiments the patient may write the time and day that the symptom occurred allowing the time and date to be stored with symptom data retrospectively.

The patient may also use the pen to record times and dosages that a medication is taken or record daily measurements that the patient performs such as patient weight measurements, blood pressure, blood sugar, or other the like. Other handwritten data that may be of interest includes dietary information, activity information, emotional information, etc. In some embodiments, the clinician may provide the patient with a check list to be used by the patient in conjunction with the digital pen. Such a check list may include symptoms that the clinician is particularly interested in monitoring. As will be further described below, the check list may be specially formatted such that checking off a particular symptom or entering data in a particular area of the paper is used during image processing performed by the digital pen for capturing the handwritten data.

At block 215, a data storage trigger signal is transmitted from the digital pen to the monitoring device. A data storage trigger signal may be transmitted upon enabling the digital pen or in response to the particular digitized handwritten data. For example, some data recorded by the digital pen, such as a serious clinical symptom, may cause the pen to generate a data storage trigger signal. Other handwritten data considered to be relatively benign, such as a daily patient weight measurement, may not cause a data storage trigger signal.

The monitoring device stores physiological signal data in response to the trigger signal at block 220. The monitoring device may be continuously monitoring a physiological signal(s) and store a snapshot of the signal(s) for a predetermined interval of time before and/or after receiving the trigger signal. If the monitoring device is not monitoring the physiological signal at the time of receiving the trigger signal, the monitoring device first enables physiological signal sensing. Additionally or alternatively, the monitoring device may deliver or adjust a therapy in response to specific data or a trigger signal received from the digital pen. For example, handwritten data transferred from the digital pen to the monitoring device corresponding to a severe or disabling symptom may cause the monitoring device to deliver or alter a therapy.

At block 225, the digitized handwritten data recorded by the digital pen is aggregated with data stored by the monitoring device, which may include both physiological data and device-related data, for example pertaining to therapy delivery operations or device diagnostics. Data aggregation includes chronologically aligning handwritten data with the physiological data and/or device-related data stored by the monitoring device. Data acquired by the digital pen and data acquired by the monitoring device can then be presented to a clinician in a unified format allowing the clinician to relate symptomatic or other handwritten data to physiological signals or other device-related data.

Data aggregation performed at block 225 is performed by a control module included in the monitoring system. Data aggregation may be performed by an implantable or external monitoring device after transmitting data from the digital pen to the monitoring device. In an alternative embodiment, data aggregation may be performed by an external device such as a home monitor or programmer after receiving the data from the digital pen and an IMD. In still other embodiments, data aggregation may be performed by a networked central database in a remote patient monitoring system after data from the digital pen and an implantable or external monitoring device have been transferred to the central database.

Before or after data aggregation, the data from the digital pen and the monitoring device may be transferred to a central database at block 230 when the monitoring device is included in a remote patient management system.

The aggregated data is presented to a physician at block 235 or may be automatically analyzed by an expert system (clinical decision support system) and, depending on its outcome, a physician may be alerted. The data may be presented on the display of a computer networked with the central database, on the display of an external programmer, printed or otherwise presented in a graphical or textual manner. The display of the aggregated data that has been aligned chronologically allows the physician to identify temporal correlations between handwritten data and data automatically acquired by the monitoring device.

Figure 5:
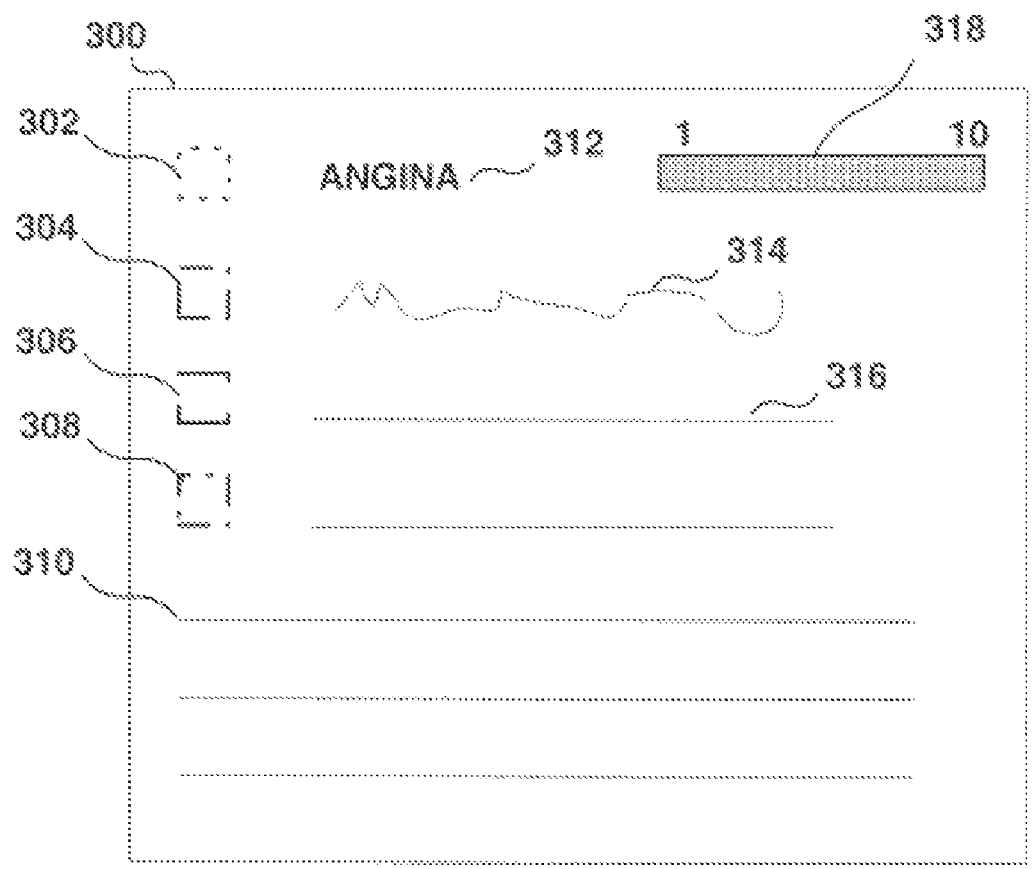
FIG. 5 is a schematic drawing of custom paper for use with a digital pen for capturing handwritten medical information in a patient monitoring system.

FIG. 5 is a schematic drawing of custom paper 300 for use with a digital pen for capturing handwritten medical information in a patient monitoring system. Paper 300 may be pre-printed with a custom pattern that is used by the image capture and processing circuitry included in the digital pen, for example the type of custom paper available from Anoto, Lund, Sweden. Paper 300 further includes pre-printed, specially formatted areas for facilitating the recordation and digital capture of handwritten medical data. A number of check boxes 302 through 308 are shown. Each check box 302 through 308 is provided as a unique identifier which may be assigned to a particular medical parameter, e.g. a particular symptom. Check boxes 302 through 308 are shown each having a unique line pattern, however in other embodiments, check boxes 302 through 308 may be color-coded, have different shapes, different shading, or other distinguishing characteristics.

In some embodiments, paper 300 is provided with a pre-printed parameter 312 assigned to one or more of the unique identifier check boxes 302. In the example shown, paper 300 is provided with a symptom label "Angina" corresponding to check box 302. Other symptom labels may be pre-printed adjacent to each check box 302 through 308, such as dizziness, shortness of breath, swelling, nausea, etc.

In other embodiments, each check box 302 through 308 may be manually labeled by a clinician or patient. A handwritten label 314 may be digitally captured by the digital pen such that the pen learns that the corresponding check box 304 is assigned to the handwritten label 314. For example, a clinician or patient may write the label using readable ink then position the digital pen nib at check box 304, without leaving ink but allowing the pen to capture an image of check box 304 thereby assigning check box 304 to the handwritten label. Additional blank lines 316 may be provided for assigning additional check boxes 306 and 308 by handwriting a label and capturing an image of the handwritten label.

Alternatively, blank lines 316 may be filled in by a physician or patient and the assigned symptom may be programmed into an associated monitoring device. For example, a physician may select symptoms to be monitored by the patient, fill in paper 300 with the list of symptoms by labeling each unique check box 302 through 308 with a symptom, then program the monitoring device to recognize a data signal corresponding to a particular check box to be associated with the manually labeled symptom.

When the patient wants to record the occurrence of a symptom, the patient need only point the digital pen at the corresponding check box 302 through 308 without having to write out the complete name of the symptom. Once the identifiable check box is assigned to a particular symptom, the digital pen need only capture an image of the unique identifier (check box) to record the occurrence of the associated symptom. Thus, the patient may not need to leave ink or other readable mark on the paper 300 allowing the same paper 300 to be used repeatedly. Paper 300 may further include pre-printed scales 318 to allow the patient to record the severity of the symptom. The patient may make a mark or merely point at a location along scale 318 using the nib of the digital pen to indicate the severity of the symptom. Scale 318 may be color-coded or formatted in other ways, e.g. through shading or unique patterns to allow the digital pen to recognize the location along scale 318 that the patient is pointing at.

Other areas of paper 300 may be left unformatted or may include blank lines 310 to allow the patient to make other handwritten notes relating to symptoms or other medical information not identified in a pre-printed area of paper 300. For example, the patient may record details regarding a symptom such as the severity of the symptom, the time of the symptom if the symptom is not presently occurring, the location of the symptom, what the patient was doing at the time the symptom occurred, etc.

Thus, a patient monitoring system and method have been presented in the foregoing description with reference to specific embodiments. It is appreciated that various modifications to the referenced embodiments may be made without departing from the scope of the invention as set forth in the following claims.

The invention claimed is:

1. A medical device system, comprising:
a monitoring device for storing data relating to a patient;
a digital pen for digitizing and storing data handwritten by the patient with the digital pen and having a real-time clock for logging the time and date of the data that has been digitized; and
a control module configured to aggregate data stored by the monitoring device and handwritten data stored by the digital pen, wherein the aggregation of the data stored by the monitoring device and the handwritten data stored by the digital pen includes chronologically aligning the handwritten data with the monitored device data based on the time and date stamp.

2. The medical device system of claim 1 wherein the digital pen comprises an image capture module for capturing an image of handwritten data.

3. The system of claim 2 further comprising a paper for use with the digital pen, the paper being formatted in at least one area for recognition of medical data using at least one unique identifier preprinted on the paper.

4. The system of claim 3 wherein the at least one unique identifier corresponds to a patient symptom.

5. The system of claim 3 wherein the control module being programmable and the at least one unique identifier being programmably assigned to a medical parameter.

6. The system of claim 5 wherein programmably assigning the unique identifier includes capturing handwritten data corresponding to the medical parameter.

7. The medical device system of claim 1 wherein the digital pen comprises a data conversion module for converting digitized data to a character encoded format.

8. The medical device system of claim 1 wherein the digital pen comprises a communication module configured for bidirectional communication with the control module for transferring the stored handwritten data to the control module.

9. The system of claim 8 wherein the monitoring device comprises a communications module configured for bidirectional communication with the digital pen and wherein the monitoring device being configured to store data in response to receiving a signal from the digital pen.

10. The system of claim 8 wherein the monitoring device comprises a communications module configured for bidirectional communication with the digital pen and further comprises a therapy delivery module responsive to handwritten data received from the digital pen.

11. The system of claim 1 wherein the monitoring device comprises a sensor for sensing a physiological signal and the data stored by the monitoring device includes physiological signal data.

12. The system of claim 1 wherein the monitoring device comprises a therapy delivery module and the data stored by the monitoring device includes therapy delivery data.

13. The system of claim 1 wherein the monitoring device being configured to perform device diagnostic tests and the data stored by the monitoring device includes device-related diagnostic data.

14. The system of claim 1 wherein the monitoring device being an implantable medical device.

15. The system of claim 14 further comprising an external device, the external device including an external communication module;
wherein the control module being included in the external device;
wherein the implantable medical device comprises an implantable communications module in communication with the external communication module for transmitting the stored data to the control module and the digital pen comprises a communication module in communication with the external device for transferring the stored handwritten data to the control module.

16. The system of claim 1 wherein the control module being included in the monitoring device.

17. The system of claim 1 further comprising a networked central database and wherein the control module being in communication with the networked central database and configured to transfer aggregated data to the networked central database.

18. A method for monitoring a patient, comprising:
digitizing data handwritten by the patient using a digital pen;
using a real-time clock for logging the date and time of the data that has been digitized;
storing data acquired by a monitoring device, and
aggregating the handwritten data with the stored data, wherein aggregating the handwritten data with the stored data includes chronologically aligning the handwritten data with the monitored device data based on the time and date stamp.

* * * * *